United States Patent [19]
Davenport et al.

[11] Patent Number: 5,318,047
[45] Date of Patent: Jun. 7, 1994

[54] METHOD FOR CORNEAL CURVATURE VARIATION

[75] Inventors: James Davenport, Fallbrook; Bryan Loomas; Mark Mathis, both of Santa Clara; Thomas Silvestrini, Alamo, all of Calif.

[73] Assignee: KeraVision Inc., Santa Clara, Calif.

[21] Appl. No.: 59,509

[22] Filed: May 10, 1993

Related U.S. Application Data

[63] Continuation of Ser. No. 820,422, Jan. 14, 1992, abandoned.

[51] Int. Cl.$^5$ ............................................. A61F 9/00
[52] U.S. Cl. .................................... 128/898; 623/4; 606/5
[58] Field of Search .......................... 128/597–599; 606/1, 4–6; 623/4–6; 351/160 R, 176, 177

[56] References Cited

U.S. PATENT DOCUMENTS

| | | | |
|---|---|---|---|
| 4,298,004 | 11/1981 | Schachar et al. | 128/898 |
| 4,452,235 | 6/1984 | Reynolds . | |
| 4,549,529 | 10/1985 | White | 128/899 |
| 4,565,198 | 1/1986 | Koeniger | 128/898 |
| 4,607,617 | 8/1986 | Choyce | 623/5 |
| 4,646,720 | 3/1987 | Peyman et al. | 128/897 |
| 4,688,570 | 8/1987 | Kramer et al. . | |
| 4,815,463 | 3/1989 | Hanna . | |
| 4,907,587 | 3/1990 | Fedorov et al. | 128/897 |
| 4,941,093 | 7/1990 | Marshall et al. . | |
| 5,090,955 | 2/1992 | Simón . | |

FOREIGN PATENT DOCUMENTS 1597188  10/1990  U.S.S.R. ................................. 606/5

OTHER PUBLICATIONS

Hartmann Chr., et al., "Intrastromale Implantation Eines Justierbaren Kunstsoffringes Zur Hornhautrefraktionsänderung", *Kongress der Deutschen Gesellschaft fur Intraokularlinsen Implantation*, delivered by H. Freyler et al., Springer-Verlag, Wien, pp. 465–475. The corresponding English language translation of the article namely, Hartmann, Chr., et al., Intrastromal implantation of an adjustable plastic ring to alter the corneal refraction *Congress for German Society for Intraocular Lens Implantation*, delivered by H. Freyler et al., (7 pages total).

Simón, G., et al., "Long term in vivo topographic studies of gel injection adjustable keratoplasty (GIAK)" *Abstracts: The Association for Research in Vision and Ophthalmology*, Annual Meeting Abstract Issue, Sarasota, Florida, USA, May 2–May 7, 1993, p. 1248, (abstract 2679-52).

Simón, G., et al., "Refractive remodeling of the cornea by intrastromal rings" *Abstracts: Eighth International Congress of Eye Research*, Proceedings of the International Society for Eye Research, San Francisco, California, USA, Sep. 4–8, 1988, vol. V, (abstract No. 47).

Simön, G., et al., "Refractive remodeling of the cornea by intrastromal rings" *The Association for Research in Vision and Ophthalmology*, Annual Spring Meeting, Sarasota, Florida, USA, Apr. 30–May 5, 1989, p. 187, (abstract 43).

Blavatskaia, D. E. D., "The use of intralamellar homoplasty in order to reduce refraction of the eye" *Uberstzt. Aus. Oftalmol. Zh.* (1966) 7:530–537 which was apparently translated to *Arch. Soc. Ophthmol. Optom.* (1988) 6:31–325.

Primary Examiner—Lee S. Cohen
Assistant Examiner—J. P. Lacyk
Attorney, Agent, or Firm—Morrison & Foerster

[57] ABSTRACT

A method for refractive correction of the eye in order to improve the vision of the eye while not adversely affecting its natural asphericity is described. The method involves determining the amount of correction necessary, selecting an intrastromal corneal ring (ICR) of appropriate thickness to obtain the necessary correction from a selection of ICRs of varying thickness, and inserting the ICR into the corneal stroma. The method may be useful for the correction of myopia and excessive astigmatism.

18 Claims, 8 Drawing Sheets

METHOD FOR CORNEAL CURVATURE VARIATION

This application is a continuation of application Ser. No. 07/820,422, filed Jan. 14, 1992 now abandoned.

TECHNICAL FIELD

This invention is in the general field of medical technology and relates specifically to a method for varying corneal curvature in order to correct vision problems.

BACKGROUND

Anomalies in the shape of the eye can cause visual disorders. Hyperopia occurs when the eyeball is too short. In such a case, parallel rays from greater than 20 feet focus behind the retina. Myopia, on the other hand occurs when the eyeball is too long. The focus of parallel rays in this case is in front of the retina. Astigmatism is a condition in which the parallel rays of light do not come to a single point, but rather have a variable focus due to the fact that the cornea is aspherical and refracts light in a different meridian at different distances. Some degree of astigmatism is normal, but where it is too high, it must often be corrected.

Hyperopia, myopia and astigmatism are usually corrected by glasses or contact lenses. Surgical methods for the correction of such disorders have been cited in the literature and include radial keratotomy (see e.g. U.S. Pat. Nos. 4,815,463 and 4,688,570) and laser corneal oblation (see e.g. U.S. Pat. No. 4,941,093). Further, the general method of implanting rings in the corneal stroma to change the curvature of the cornea is known. Previous work involving the implantation of polymethylmethacrylate (PMMA) rings, allograft corneal tissue and hydrogels is well documented. One of the ring devices involves a ring design that allows a split ring to be inserted into a channel dissected in the stromal layer of the cornea using a minimally invasive incision through which the channel for the implant is created and through which the implant is inserted and adjusted. Adjustment of the device normally involves an adjustment of ring size or diameter.

U.S. Pat. No. 4,452,235, which is herein incorporated by reference in its entirety, describes a method and apparatus for corneal curvature adjustment. The method involves inserting one end of a split end adjusting ring into the cornea of the eye and moving the ring in a circular path until its ends meet. The ends are thereafter adjusted relative to each other until the shape of the eye has assumed a desired curvature whereupon the ends are fixedly attached to maintain the desired curvature of the cornea.

The present invention describes a method that allows for the refractive correction of the eye wherein the curvature of the cornea is changed by inserting rings of varying thickness into the corneal stroma.

DISCLOSURE OF THE INVENTION

One aspect of the invention is a method for refractive correction of an eye for the purpose of improving the vision of the eye without adversely affecting its natural asphericity. The amount of correction necessary for improving the vision of the eye is determined. Next, an intrastromal corneal ring (ICR) of a thickness that will provide the determined amount of refractive correction is selected from a plurality of rings of varying thickness. Finally, the ring is inserted into the corneal stroma of the eye.

A second aspect of the invention is a method for correcting myopia in the human eye. The amount of refractive correction necessary for correcting the myopia is determined. Next, an ICR of a thickness that will provide the determined amount of refractive correction is selected from a plurality of rings of varying thickness. Finally, the ring is inserted into the corneal stroma of the eye.

A further aspect of the invention is a method for alleviating excessive astigmatism in the human eye. The amount of refractive correction necessary for alleviating the excessive astigmatism is determined. Next, an ICR of a thickness that will provide the determined amount of refractive correction is selected from a plurality of rings of varying thickness. Finally, the ring is inserted into the corneal stroma of the eye.

BRIEF DESCRIPTION OF THE DRAWINGS

Like elements in the drawings bear the same reference numerals.

MODES FOR CARRYING OUT THE INVENTION

Figure 1:
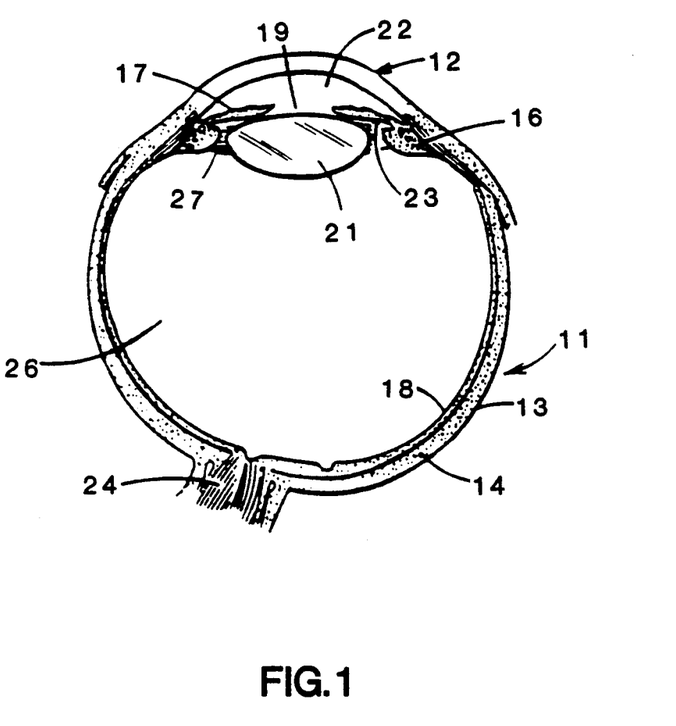
FIG. 1 is a schematic representation of a horizontal section of the eye.

FIG. 1 shows a horizontal section of the eye with the globe 11 of the eye resembling a sphere with an anterior bulged spherical portion representing the cornea 12.

The globe 11 of the eye consists of three concentric coverings enclosing the various transparent media through which the light must pass before reaching the sensitive retina 18. The outermost covering is a fibrous protective portion the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 16 and iris 17. The choroid 14 generally functions to maintain the retina 18. The ciliary body 16 is involved in suspending the lens 21 and accommodation of the lens. The iris 17 is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina 18. It contracts also to accommodation, which serves to sharpen the focus by diminishing spherical aberration. The iris 17 divides the space between the cornea 12 and the lens 21 into an anterior chamber 22 and posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body 26 is a transparent gelatinous mass which fills the posterior four-fifths of the globe 11. At its sides it supports the ciliary body 16 and the retina 18. A frontal saucer-shaped depression houses the lens.

The lens 21 of the eye is a transparent bi-convex body of crystalline appearance placed between the iris 17 and vitreous body 26. Its axial diameter varies markedly with accommodation. A ciliary zonule 27, consisting of transparent fibers passing between the ciliary body 16 and lens 21 serves to hold the lens 21 in position and enables the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
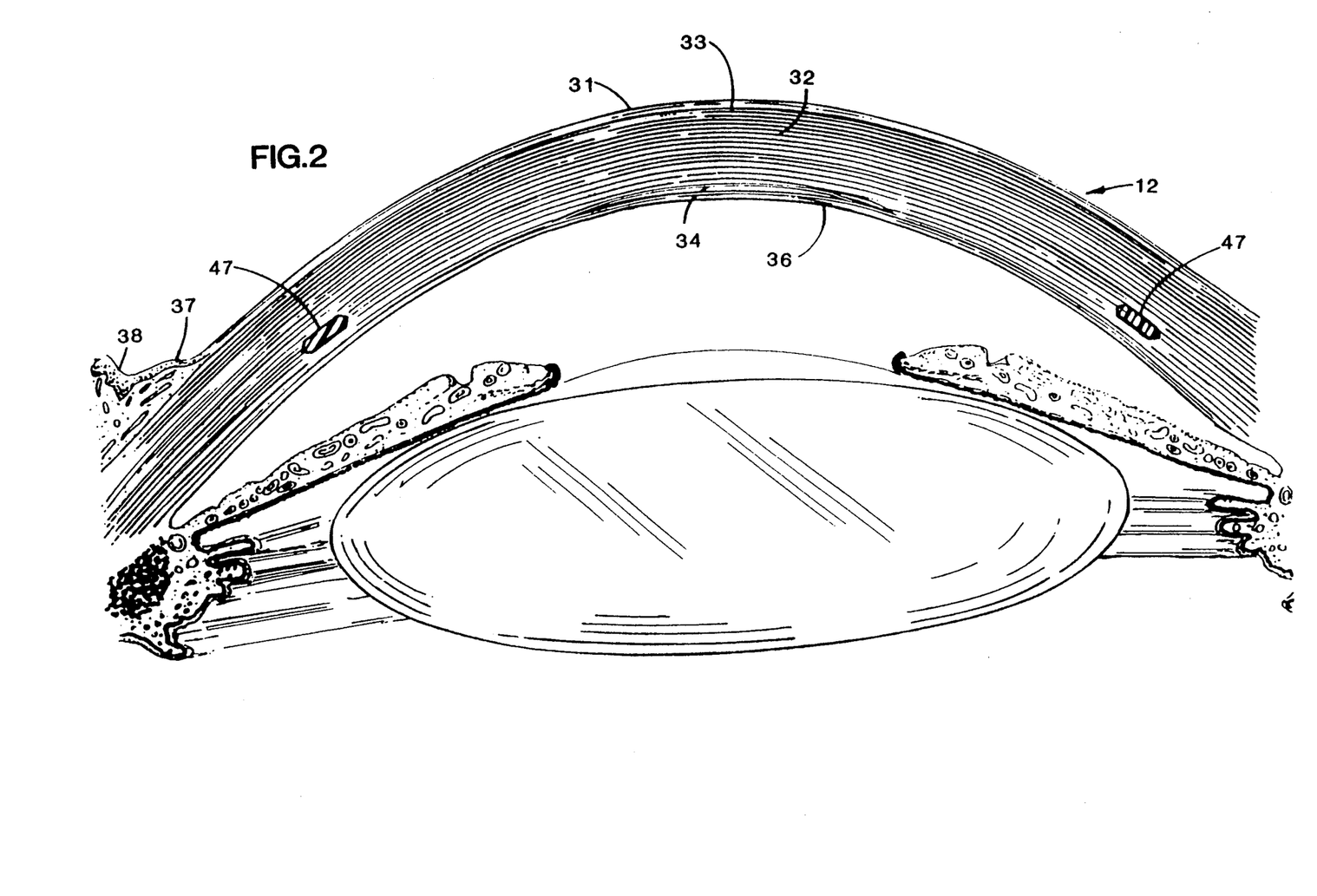
FIG. 2 is a schematic illustration of the anterior portion of the eye showing the various layers of the cornea.

Referring to FIG. 2, a more detailed drawing of the anterior portion of the globe shows the various layers of the cornea 12 comprising an epithelium 31. Epithelial cells on the surface thereof function to maintain transparency of the cornea 12. These epithelial cells are rich in glycogen, enzymes and acetylcholine and their activity regulates the corneal corpuscles and controls the transport of water and electrolytes through the lamellae of the stroma 32 of the cornea 12.

An anterior limiting lamina 33, referred to as Bowman's membrane or layer, is positioned between the epithelium 31 and the stroma 32 of the cornea. The stroma 32 is comprised of lamella having bands of fibrils parallel to each other and crossing the whole of the cornea. While most of the fibrous bands are parallel to the surface, some are oblique, especially anteriorly. A posterior limiting lamina 34 is referred to as Descemet's membrane. It is a strong membrane sharply defined from the stroma 32 and resistant to pathological processes of the cornea.

The endothelium 36 is the most posterior layer of the cornea and consists of a single layer of cells. The limbus 37 is the transition zone between the conjunctiva 38 and sclera 13 on the one hand and the cornea 12 on the other.

Figure 3:
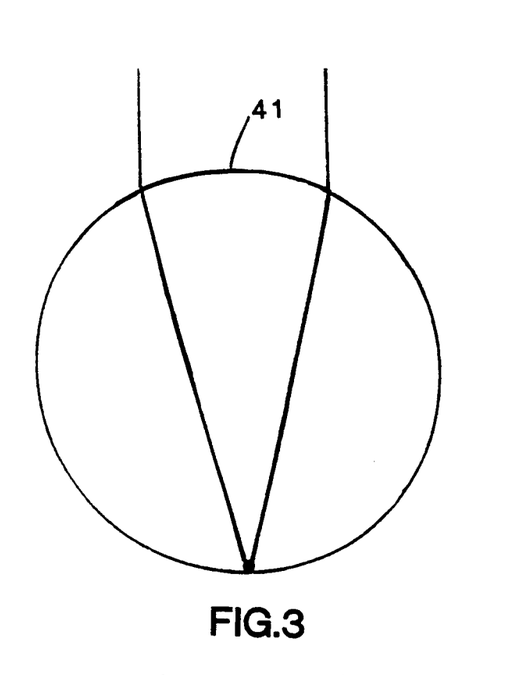
FIG. 3 is a schematic representation of a normal eye.
Figure 4:
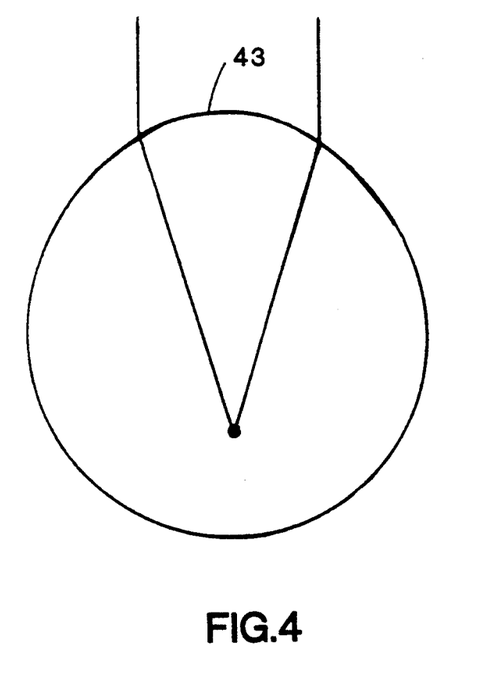
FIG. 4 is a schematic representation of a myopic eye.

FIG. 3 shows the globe of the eye having a cornea 12 with a normal curvature 41. If parallel rays of light pass through the corneal surface of FIG. 3, they are refracted by the corneal surfaces to converge eventually near the retina of the eye. The diagram of FIG. 3 discounts, for the purposes of this discussion, the refractive effect of the lens or other portions of the eye. The eye depicted in FIG. 4 is myopic. The corneal curvature 43 causes the light rays to refract into focus at a point in the vitreous body which is short of the retinal surface. If an ICR is implanted into the chord of the cornea such that the radius of curvature of the cornea is uniformly increased, the central curvature of the cornea is flattened. Light rays refracted by the now flattened corneal surface will be refracted at a smaller angle and thus converge at a more distant point such as directly on the retina.

The method of the present invention is concerned with a system for adjusting an annular chord of the cornea to increase the radius of curvature of the cornea without adversely affecting its natural asphericity. Where there is serious astigmatism, the natural asphericity will not be altered such that the astigmatism will be significantly increased. However, where there is significant astigmatism that results in impaired vision, the method of the invention may actually improve the asphericity to reduce such astigmatism and improve vision. Referring to FIG. 2, an intrastromal corneal ring (ICR) 47, having a cross sectional shape as shown in FIG. 5B is shown implanted in the stromal layer of the cornea. By selecting the thickness of the ring according to the amount of correction necessary, the rays refracted by the cornea and other eye components can be brought to focus directly on the retina 18. The thickness of the ring may be between 0.05 mm and 0.60 mm. Such a ring placed approximately at the 8 mm chord of the cornea provides a means for making such a corrective adjustment.

Figure 5A:
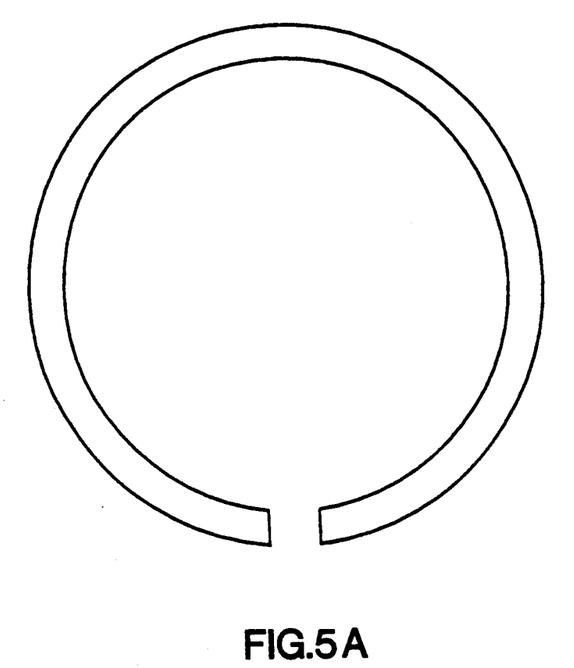
FIG. 5A is a plan view of an ICR of the invention.
Figure 5B:
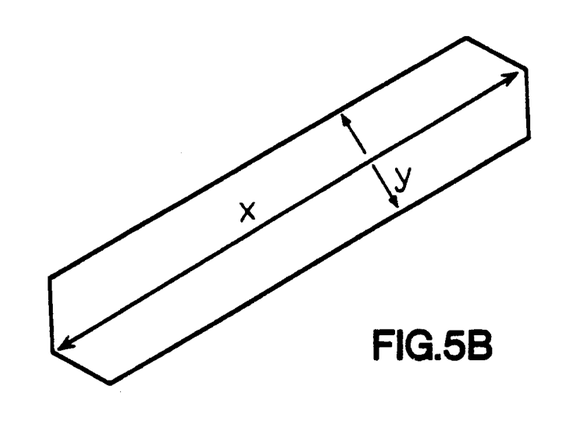
FIG. 5B is an cross sectional view of an ICR of the invention.

FIG. 5A shows a preferred ICR of the invention. The ICR is comprised of a generally circular member having split end portions. The ring is comprised of a material which has sufficient stiffness to maintain its generally circular shape. The material should have properties that render it physiologically compatible with the tissue of the cornea. An illustrative material is a plastic type material sold under the trade name of PLEXIGLASS TM, however many other biocompatible polymers are useful in the invention. The cross sectional shape of the rings is that of FIG. 5B and is generally dimensioned to be about 1 mm from point to point (dimension x) and from about 0.05 mm to 0.60 mm in thickness (dimension y).

Even where the eye is not myopic, the method of the present invention may be useful to alleviate excessive astigmatism.

In the method of the invention, the physician will determine the amount of corrective refraction necessary to improve a patient's vision. From the determination of necessary corrective refraction, the physician will choose an ICR from a panel of ICRs of varying thickness. A typical panel of ICRs will consist of 5 ICRs with the following thicknesses: 0.25 mm, 0.30 mm, 0.35 mm, 0.40 mm and 0.45 mm. The corrective refraction for those ICRs are as follows: between 1.0 and 2.0 diopters for the 0.25 mm ICR, between 2.0 and 4.0 diopters for the 0.30 mm ICR, between 4.0 and 8.0 diopters for the 0.35 mm ICR, between 6.0 and 10.0 diopters for the 0.40 mm ICR, and between 8.0 and 15.0 diopters for the 0.45 mm ICR. It should be noted that these values are for ICRs of cross sectional shape shown in FIG. 5B. The amount of corrective refraction for the various thicknesses of ICRs of different cross sectional shaped rings may differ from those values.

After the physician has selected the appropriate ICR, he/she will proceed to insert the ICR into the corneal stroma of the eye. The ICR is inserted through a 2.5 mm oblique keratotomy incision placed peripherally into the corneal stroma. Prior to ring insertion, a channeling blade is inserted at the depth of the incision and a circular channel is cut into the corneal stroma. Proper centering of the cut is accomplished by use of a centering device that aligns the channeling blade. The ring is then inserted and the ends are secured by fastening one end to the other.

The following examples are intended to further illustrate but not to limit the invention in any manner.

EXAMPLE 1

Figure 6:
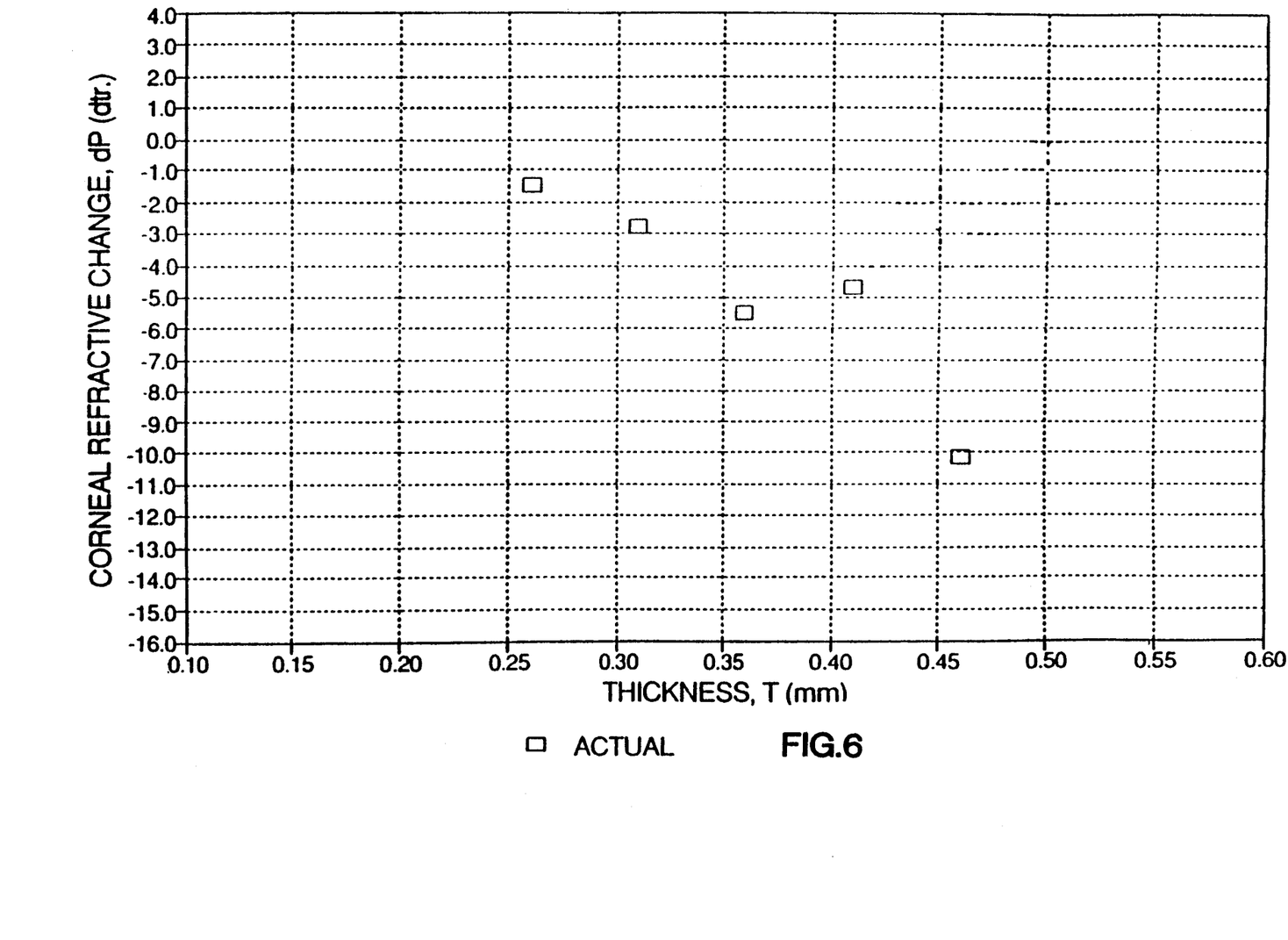
FIG. 6 shows the effect of ICR thickness on refraction.

In order to define the corneal topography that results from the ICR thickness effect, ICR's of 0.26, 0.31, 0.36, 0.41 and 0.46 mm thickness were implanted into deturgesced cadaver eyes. The average spherical radii of curvature were measured using a Kerametrics Class II Corneal Surface Analyzer which uses laser holographic interferometry to measure corneal topography. The results of this study are shown in FIG. 6. Excluding the data from the 0.41 ICR wherein an air bubble artifact was discovered, the corneal flattening relationship is approximately linear. That is, there is approximately 1 diopter of flattening for each 0.02 mm increase in ICR thickness for the given range of ICR sizes.

EXAMPLE 2

Figure 7A:
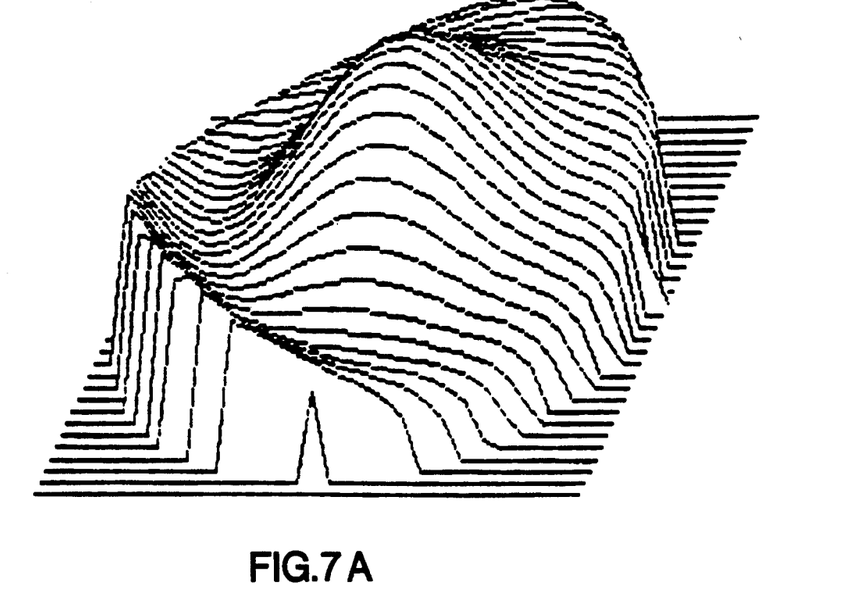
FIGS. 7A, 7B, 7C and 7D show the change in asphericity when an ICR is implanted into a cadaver eye.
Figure 7B:
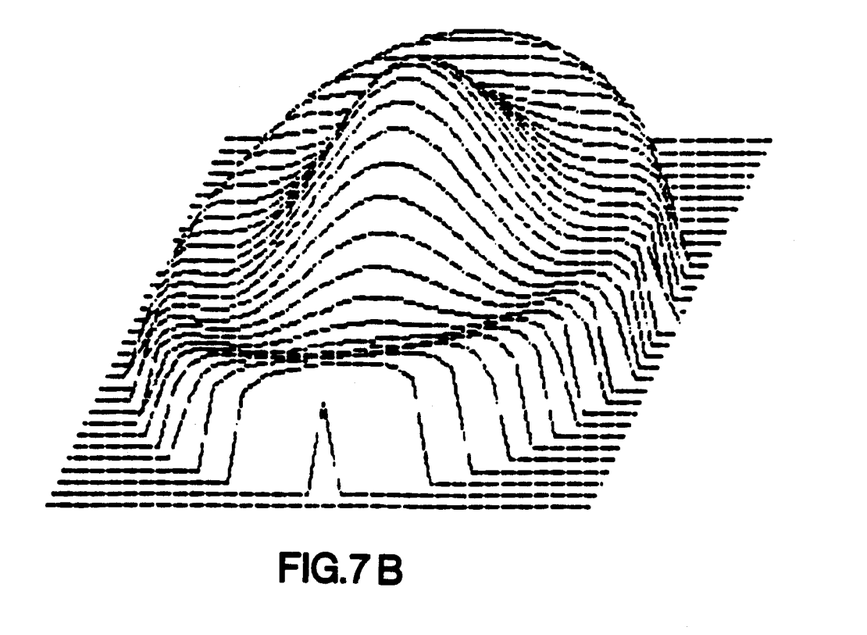
Figure 7C:
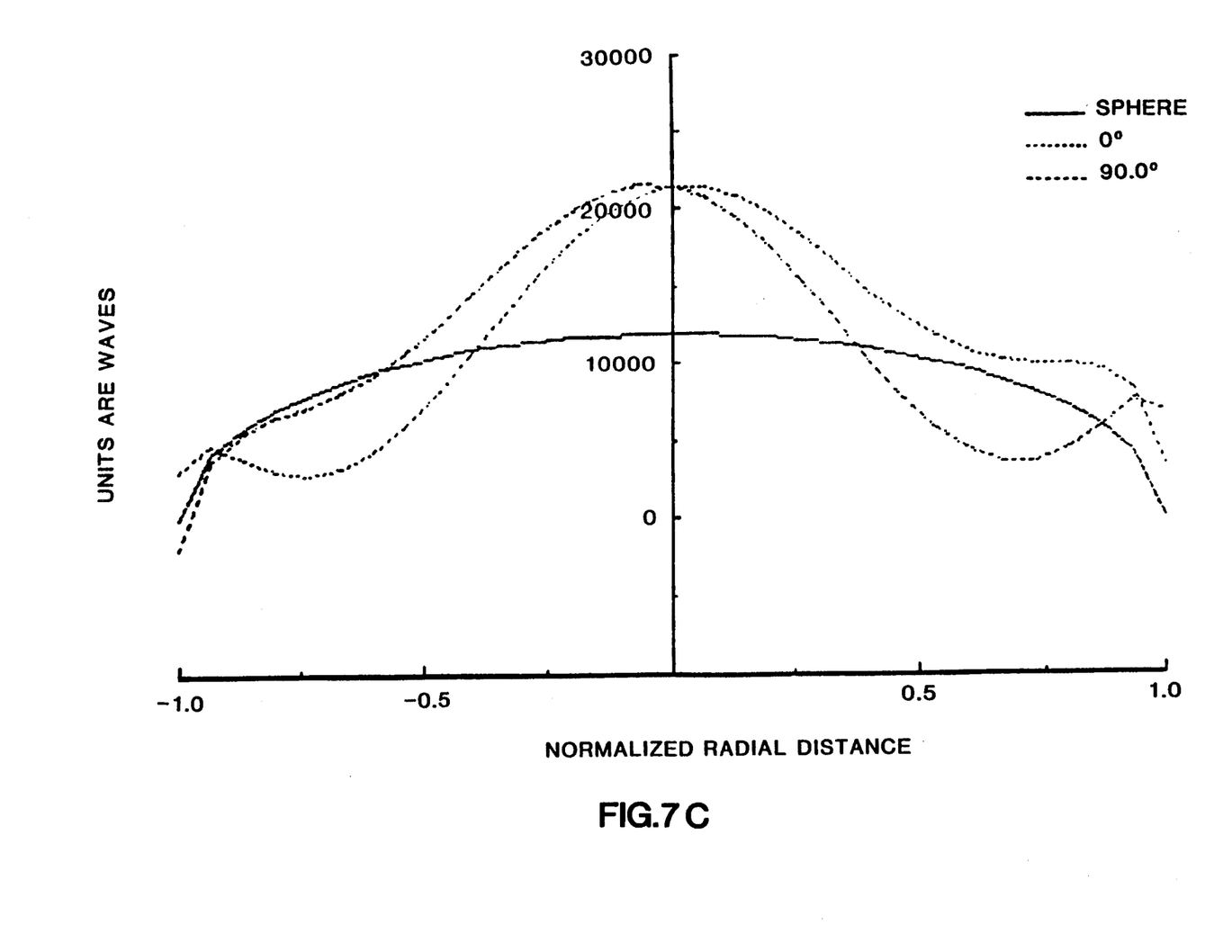
Figure 7D:
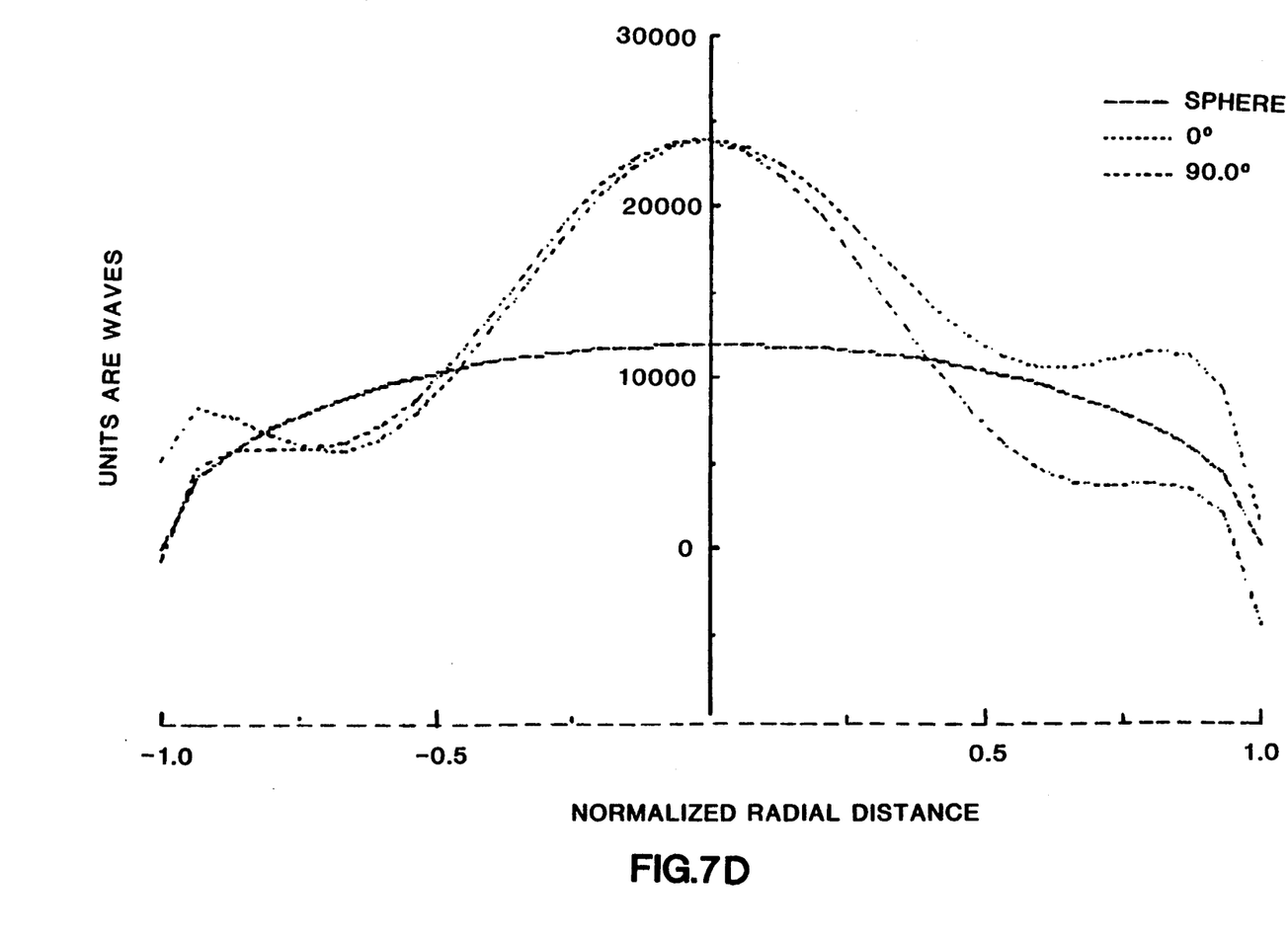

In order to determine the effect of ICR's on the natural asphericity of the cornea, the corneal topography of an eye was measured before and after ICR implantation using the Kerametrics Class II Corneal Surface Analyzer. The Analyzer uses laser holographic interferometry to measure corneal topography. The results of these measurements are presented in units of waves of deviation from spherical in FIGS. 7A, 7B, 7C, and 7D for an ICR of 0.30 mm thickness. These curves exaggerate the topographical deviations from a spherical surface yet measure the entire corneal surface to a high degree of accuracy. The measurement of the cornea before and after implantation of the ICR indicates that the natural asphericity of the cornea is not eliminated and that the central portion of the cornea becomes more symmetrical as indicated by the profiles measured at 0 degrees (the top of the cornea) and a point 90 degrees removed. FIGS. 7A and 7B show the cornea of a cadaver prior to ICR implantation. FIGS. 7C and 7D show the same cornea after implantation of an ICR of 0.30 mm thickness.

EXAMPLE 3

Four human patients were implanted with 0.30 mm intrastromal corneal rings. The visions of the patients prior to surgery were measured to be: 20/400, 20/400, 20/200, and 20/400. Twelve hours following surgery the visions had improved to 20/15, 20/30, 20/40, and 20/30. There was no serious trauma to the eyes of any of the four patients.

Modifications of the above described modes for carrying out the invention that are obvious to persons of skill in the fields of medicine, ophthalmology, optometry and/or related fields are intended to be within the scope of the following claims.

We claim:

1. A method for refractive correction of a human eye for the purpose of improving the vision of said eye without adversely affecting its natural asphericity, said method comprising:
    (a) determining an amount of refractive correction necessary for improved vision in said eye;
    (b) providing a plurality of intrastromal corneal rings (ICRs) of varying thickness;
    (c) selecting from said plurality of ICRs an ICR of a thickness that provides said amount of refractive correction; and
    (d) inserting the selected ICR into the corneal stroma of said eye.
2. The method of claim 1 wherein the thickness of the ICR is between 0.05 and 0.60 mm.
3. The method of claim 1 wherein the refractive correction is between 1.0 and 18.0 diopters.
4. The method of claim 1 wherein the refractive correction is between 1.0 and 2.0 diopters and the ICR is 0.25 mm thick.
5. The method of claim 1 wherein the refractive correction is between 2.0 and 4.0 diopters and the ICR is 0.30 mm thick.
6. The method of claim 1 wherein the refractive correction is between 4.0 and 8.0 diopters and the ICR is 0.35 mm thick.
7. The method of claim 1 wherein the refractive correction is between 6.0 and 10.0 diopters and the ICR is 0.40 mm thick.
8. The method of claim 1 wherein the refractive correction is between 8.0 and 15.0 diopters and the ICR is 0.45 mm thick.
9. A method for correcting myopia in a human eye, said method comprising:
    (a) determining an amount of refractive correction necessary to correct said myopia;
    (b) providing a plurality of intrastromal corneal rings (ICRs) of varying thickness;
    (c) selecting from said plurality of ICRs an ICR of a thickness that provides said amount of refractive correction; and
    (d) inserting the selected ICR into the corneal stroma of the eye.
10. The method of claim 9 wherein the thickness of the ICR is between 0.05 and 0.60 mm.
11. The method of claim 9 wherein the refractive correction is between 1.0 and 18.0 diopters.
12. The method of claim 9 wherein the refractive correction is between 1.0 and 2.0 diopters and the ICR is 0.25 mm thick.
13. The method of claim 9 wherein the refractive correction is between 2.0 and 4.0 diopters and the ICR is 0.30 mm thick.
14. The method of claim 9 wherein the refractive correction is between 4.0 and 8.0 diopters and the ICR is 0.35 mm thick.
15. The method of claim 9 wherein the refractive correction is between 6.0 and 10.0 diopters and the ICR is 0.40 mm thick.
16. The method of claim 9 wherein the refractive correction is between 8.0 and 15.0 diopters and the ICR is 0.45 mm thick.
17. A method for alleviating excessive astigmatism in a human eye said method comprising:
    (a) determining an amount of refractive correction necessary for alleviating the excessive astigmatism in said eye;
    (b) providing a plurality of intrastromal corneal rings (ICRs) of varying thickness;
    (c) selecting from said plurality of ICRs an ICR of a thickness that provides said amount of refractive correction; and
    (d) inserting the selected ICR into the corneal stroma of the eye.
18. The method of claim 17 wherein the intrastromal corneal ring has a thickness of between about 0.05 and 0.60 mm.

* * * * *